United States Patent [19]
Stubbs

[11] Patent Number: 5,485,853
[45] Date of Patent: Jan. 23, 1996

[54] APPARATUS FOR WITHDRAWING FLUID OR TISSUE FROM A PATIENT'S BODY

[76] Inventor: George Stubbs, 8978 Wonderland Park Ave., Los Angeles, Calif. 90046

[21] Appl. No.: 233,413

[22] Filed: Apr. 28, 1994

[51] Int. Cl.$^6$ .................................................. A61B 10/00
[52] U.S. Cl. ........................... 128/752; 128/765; 604/220
[58] Field of Search ........................... 128/760, 763–766, 128/770; 604/207–211, 220, 228

[56] References Cited

U.S. PATENT DOCUMENTS

| | | |
|---|---|---|
| 391,414 | 10/1888 | Howell . |
| 3,747,812 | 7/1973 | Karman et al. . |
| 4,141,360 | 2/1979 | Lasswell . |
| 4,287,819 | 9/1981 | Emerit . |
| 4,318,414 | 3/1982 | Schuster et al. ........................ 128/759 |
| 4,592,746 | 6/1986 | Burkholder et al. .................... 604/220 |
| 4,610,672 | 9/1986 | Ewalt et al. ............................ 604/220 |
| 4,642,102 | 2/1987 | Ohmori .................................. 604/210 |
| 4,711,637 | 12/1987 | Leigh et al. ............................ 604/220 |
| 4,758,232 | 7/1988 | Chak ...................................... 604/220 |
| 4,890,626 | 1/1990 | Wang ...................................... 128/752 |
| 4,950,163 | 8/1990 | Zimble ................................... 433/215 |
| 4,958,622 | 9/1990 | Selenke ................................. 128/765 |
| 5,135,511 | 8/1992 | Houghton et al. ...................... 604/220 |
| 5,215,536 | 6/1993 | Lampropoulos et al. ............... 604/220 |
| 5,242,400 | 9/1993 | Blake, III et al. ....................... 604/110 |
| 5,246,011 | 9/1993 | Caillouette ............................. 128/753 |
| 5,263,934 | 11/1993 | Haak ...................................... 604/220 |

Primary Examiner—Max Hindenburg
Attorney, Agent, or Firm—Ellsworth R. Roston; Charles H. Schwartz

[57] ABSTRACT

One end of a hollow cylindrical tube is attached to a tubing positionable in a patient's body. A radial flange on the tube supports a collar in abutting relationship to one flange surface. Lugs extend integrally from the collar through the flange for disposition against the opposite flange surface. The collar extends radially past the tube's inner periphery and has slots at its inner periphery. Stops integral with the inner periphery of the collar are annularly displaced relative to the slots. Ramps on the collar lead to the stops. A piston in the tube along part of its length has, at the end within the tube, a sleeve in sealed relationship with the tube is inner periphery. Splines have grooves at spaced positions along their axial lengths at the radially outer ends of the splines. A handle at the piston axial end has an aperture to receive a user's finger for manual adjustment of the piston axially relative to the tube. In use, the piston is withdrawn axially within the tube to create a vacuum for sucking fluid or tissue from the patient's body into the tube. This piston withdrawal continues until one set of the spline grooves becomes aligned with the collar slots. The piston is then rotated to dispose the splines against the stops. In this position, the piston cannot be rotated or moved axially because of the non-alignment between the spline grooves and the collar slots. This causes the fluid to be retained within the tube.

21 Claims, 1 Drawing Sheet

APPARATUS FOR WITHDRAWING FLUID OR TISSUE FROM A PATIENT'S BODY This invention relates to apparatus for withdrawing fluids or tissue from a patient's body such as from a patient's body so that the fluid can be tested for various properties. The invention particularly relates to apparatus which is simply constructed and simply operated to withdraw fluid or tissue from a patient's body such as from a patient's body.

A wide variety of apparatus is now in use in the medical field for removing fluids or tissue from a patient to perform tests on such fluid or tissue. For example, apparatus is now in use for removing fluid or tissue from a patient by a vacuum or suction. In such apparatus, a piston is moved in a hollow tube or cylinder to create a vacuum in the cylinder for withdrawing the fluid or tissue from a patient's body into the tube or cylinder. Such apparatus is generally quite complicated in construction and is thus quite expensive. Such apparatus is sometimes undesirable because it does not hold the withdrawn fluid or tissue in a sealed relationship within the tube or cylinder. A need has thus existed for a long period of time to provide apparatus which is simply constructed and reliable in operation and which withdraws fluid or tissue efficiently from a patient's body and holds the fluid or tissue after such withdrawal.

This invention provides apparatus which withdraws a fluid or tissue from a patient's body as by a vacuum or suction created as a result of a movement of a piston within a tube or cylinder. The apparatus retains the fluid or tissue in a sealed relationship within the tube or cylinder so that the fluid or tissue will be available for subsequent testing. The apparatus is advantageous because it is simple in construction and easy and reliable in operation.

In one embodiment of the invention, one end of a hollow cylindrical tube is attached to a tubing positionable in a patient's body. A radial flange on the tube supports a collar in abutting relationship to one surface of the flange. Lugs extend integrally from the collar through the flange for disposition against the opposite flange surface. The collar extends radially past the tube's inner periphery and has slots at its inner periphery. Stops integral with the inner periphery of the collar are annularly displaced relative to the slots. Ramps on the collar lead to the stops.

A piston in the tube along part of its length has, at the end within the tube, a sleeve in sealed relationship with the tube's inner periphery. Splines have grooves at spaced positions along their axial lengths at the radially outer ends of the splines. A handle at the axial end of the piston opposite the sleeve has an aperture to receive a user's finger for manual adjustment of the piston axially relative to the tube.

In use, the piston is withdrawn axially within the tube to create a vacuum for sucking fluid or tissue from the patient's body into the tube. This piston withdrawal continues until one set of the spline grooves becomes aligned with the collar slots. The piston is then rotated to dispose the splines against the stops. In this position, the piston cannot be rotated or moved axially because of the non-alignment between the spline grooves and the collar slots. This causes the fluid to be retained within the tube.

The apparatus of this invention has certain important advantages in addition to those discussed above. It eliminates the need for a suction pump. It produces little, if any, noise even during operation, thereby minimizing apprehension on the part of the patient. It can be pre-packaged in a sterile atmosphere and can be removed from the package only in the operating room. There is accordingly no need to clean tubing or bottles. It can be easily and efficiently used in a doctor's office as well as in a hospital.

Figure 1:
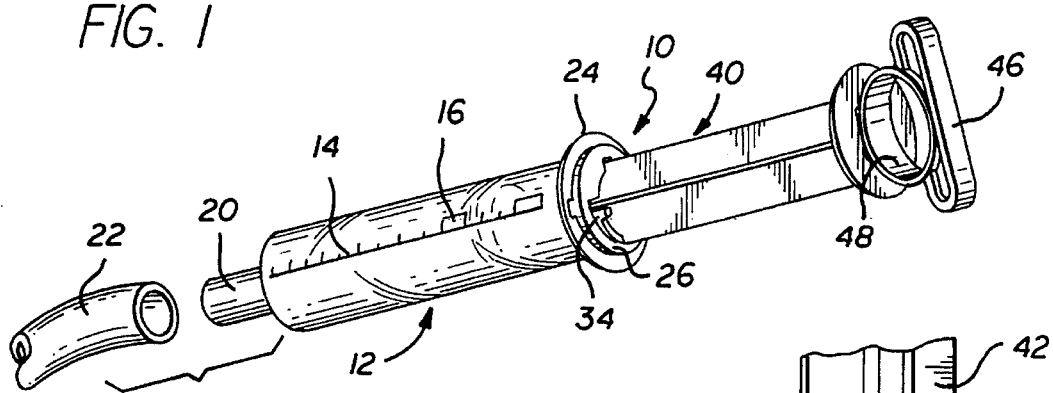
FIG. 1 is a perspective view of apparatus constituting one embodiment of the invention for withdrawing fluid or tissue from a patient's body and for holding the fluid or tissue in a sealed relationship after such withdrawal.
Figure 2:
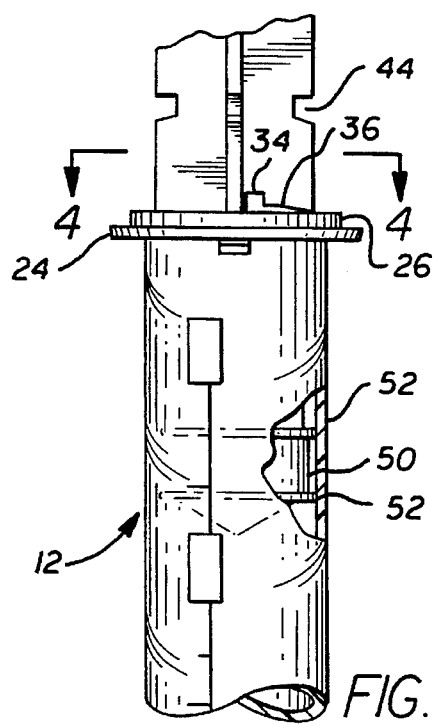
FIG. 2 is an enlarged fragmentary front elevational view of the apparatus shown in FIG. 1 when a piston is in one axial and rotational position in a hollow tube, this axial and rotational position providing for a further axial movement of the piston in the hollow tube.
Figure 3:
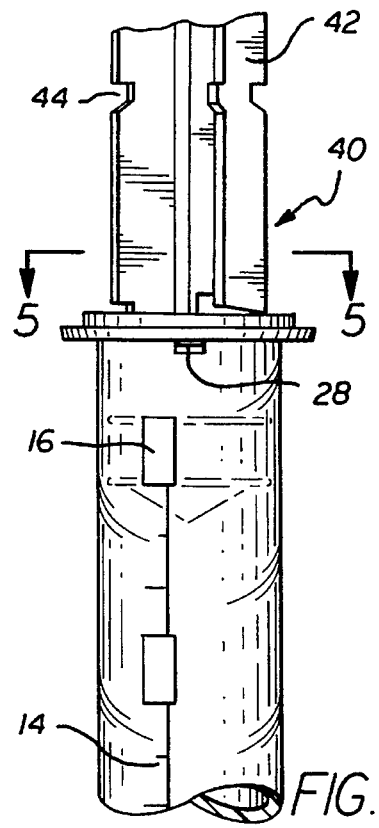
FIG. 3 is an enlarged fragmentary front elevational view of the apparatus shown in FIG. 1 when the piston is in an axial and rotational position in the hollow tube to prevent any further axial movement of the piston in the tube and to retain in the tube the fluid or tissue withdrawn from the patient's body.
Figure 4:
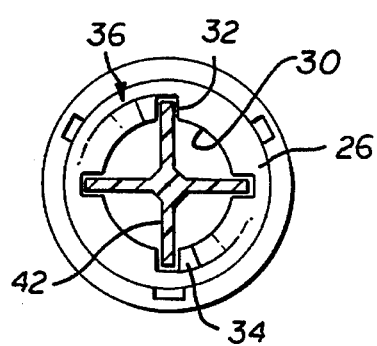
Figure 5:
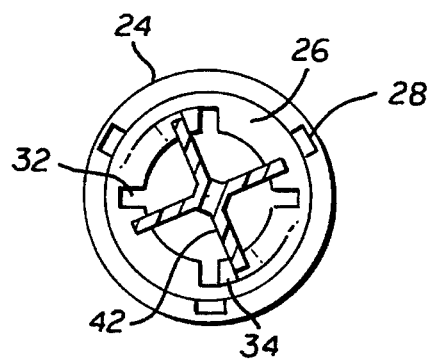

FIG. 4 is a sectional view substantially on the line 4—4 of FIG. 2 and shows additional features of the piston and a collar on the piston in the axial and rotational disposition of the piston providing for a further axial movement of the piston in the hollow tube; and FIG. 5 is a sectional view substantially on the line 5—5 of FIG. 3 and shows additional features of the piston and the collar in the axial and rotational disposition of the piston preventing further axial movement of the piston in the tube.

Apparatus generally indicated at 10 is shown in the drawings for withdrawing fluid or tissue from a patient's body and for retaining the fluid in a sealed relationship after withdrawal. The apparatus 10 includes a hollow tube 12 generally having a cylindrical configuration and made from a suitable material such as a polyethylene. The tube 12 may be made from a suitable material such as a polyethylene. Progressive numerical indications of the amount of fluid or tissue withdrawn into the tube 10 may be provided in a scale as at 14. A pair of selective values on the scale 14 have individual markings as at 16. One end of the tube 12 is tapered as at 20 to receive tubing 22. The tubing 22 may be provided with a cutting edge (not shown) at its outer extremity to remove tissue from a patient's body (e.g. a patient's uterus).

The tube 12 has at one end a flange 24 which extends radially from the tube. A collar 26 made from a suitable material such as a polyethylene is disposed on the flange with one face of the collar disposed against one surface of the flange. Lugs 28 extend integrally from the collar 26 through openings in the flange 24. The lugs 28 are folded against the opposite surface of the flange 24 to retain the collar 26 in fixed position against the flange.

The collar 24 is open at its inner periphery 30 which is disposed radially below the inner periphery of the tube 12. Slots 32 (FIGS. 4 and 5) are provided at spaced angular positions radially interior to the inner periphery of the tube 12. Stops 34 are disposed on the surface of the collar 26 displaced from the flange 24, preferably at positions contiguous to the slots 32. Ramps 36 extend progressively from the surface of the collar 26 toward the stops 34.

A piston Generally indicated at 40 is disposed partially in the tube 12. The piston 40 may be made from a suitable material such as a polyethylene. The piston 40 has splines 42 which extend radially outwardly from the piston. Grooves 44 are disposed in the splines 42 at spaced positions in the axial direction. The widths of the grooves 44 are slightly greater than the thickness of the collar 26. A handle 46 is disposed on the piston 40 at the end of the piston external to the tube 12. The handle 46 has an opening 48 for receiving a finger of a user to facilitate the movement of the piston 40 in the axial direction.

A sleeve 50 made from a resilient material such as a rubber is disposed on the end of the piston 40 within the tube 12. The sleeve 50 has, at its opposite ends in the axial direction, flanges 52 which engage the inner periphery of the tube 12 and produce a seal with such tube periphery in any axial or rotational disposition of the piston.

In use, the tubing 22 is disposed in a patient's body such as a patient's uterus. The piston 40 is then moved axially in a direction to move the sleeve 50 toward the collar 26. This creates a vacuum or a suction force in the tube 12 to withdraw fluid or tissue from the patient's body (e.g. the patient's uterus) into the tube. For example, tissue may be drawn into the tube 12 from a patient's body to provide a histological diagnosis of dysfunctional uterine bleeding. Other uses of the apparatus 10 are illustratively for menstrual extraction, outpatient D and C and an incomplete abortion.

When the grooves 44 in the splines 42 become axially aligned with the slots 32 in the collar 30 during the movement of the sleeve 50 toward the collar 26, the axial movement of the piston 40 may be discontinued. This alignment may be indicated by the disposition of the sleeve 50 above the markings 16 when the tube 12 is made from a clear plastic material. The piston 40 may then be rotated so that the splines 42 become disposed against the stops 34. The rotation of the piston 40 occurs from the position shown in FIGS. 2 and 4 to the position shown in FIGS. 3 and 5. With the piston 40 in the position shown in FIGS. 3 and 5, any fluid or tissue in the tube 12 is retained for subsequent testing.

The apparatus described above has certain important advantages. It can be pre-sterilized and pre-packaged. It can be brought into the operating room and the package can be opened under sanitary conditions. When the package is opened, it can be used without producing any sounds which would create apprehension in the mind of the patient. It can be used relatively easily and efficiently to collect a sample of fluid and tissue from the patient's body and then it can be further operated to retain the fluid or tissue in the hollow tube 12.

When the apparatus has been used and the fluid or tissue has been removed from the hollow tube 12, the apparatus can be discarded. The apparatus of this invention is efficient, particularly since it involves only one (1) movable part to perform two (2) successive functions. Partly because the apparatus has only one (1) moving part, it can be made economically. Furthermore, it is relatively compact so that it can be easily stored. It is also light in weight. This facilitates the ease with which the apparatus can be operated to withdraw the fluid or tissue into the tube 12.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination, a hollow tube, a collar fixedly disposed on the tube and having an inner periphery and having slots extending radially outwardly from its inner periphery at annularly spaced positions around its inner periphery, stops disposed on the collar and extending in an axial direction, ramps extending from the collar to the stops, and a piston disposed within the hollow tube for axial movement within the tube and extending axially from the tube and having radially disposed splines disposed in cooperative relationship with the radially disposed slots in the collar to provide for an axial movement of the piston within the tube when the splines are aligned with the slots in the collar, the splines being grooved to provide for a rotational movement of the piston on the ramps, with the grooves in the piston splines axially aligned with the collar, to dispose the splines against the stops in the collar for a locking relationship, between the collar and the splines.

2. In combination, a hollow tube, a collar disposed on the tube and having radially disposed slots at annularly spaced positions around its inner periphery, stops disposed on the collar and extending in an axial direction, ramps extending from the collar to the stops, and a piston disposed within the hollow tube for axial movement within the tube and extending axially from the tube and having splines disposed in cooperative relationship with the radially disposed slots in the collar to provide for an axial movement of the piston within the tube when the splines are aligned with the slots in the collar, the splines being grooved to provide for a rotational movement of the piston on the ramps, with the grooves in the piston splines axially aligned with the collar, to dispose the splines against the stops in the collar for a locking relationship between the collar and the splines, means disposed at the end of the piston external to the piston for facilitating the manual gripping of the piston to move the piston relative to the hollow tube, the stops being disposed on the collar externally of the collar.

3. In a combination as set forth in claim 2, a sleeve made from a resilient material and movable with the piston within the hollow tube to receive fluid within the tube as a result of the axial movement of the piston within the tube and to retain such fluid within the tube, the stops on the collar extending through the tube from a position external of the tube to retain the collar fixedly on the tube.

4. In combination, a hollow tube, a collar disposed on the tube and having radially disposed slots at annularly spaced positions around its inner periphery, stops disposed on the collar and extending in an axial direction, and a piston disposed within the hollow tube for axial movement within the tube and extending axially from the tube and having splines disposed in cooperative relationship with the radially disposed slots in the collar to provide for an axial movement of the piston within the tube when the splines are aligned with the slots in the collar, the splines being grooved to provide for a rotational movement of the piston on the collar, with the grooves in the piston splines axially aligned with the collar, to dispose the splines against the stops in the collar for a locking relationship between the collar and the splines means disposed at the end of the piston external to the piston for facilitating the manual gripping of the piston to move the piston relative to the hollow tube, a sleeve made from a resilient material and movable with the piston within the hollow tube to receive fluid within the tube as a result of the axial movement of the piston within the tube and to retain such fluid within the tube, the tube having a radial flange, the collar being disposed on one axial side of the axial flange, and a lug integral with the collar and extending through the tube to the opposite axial side of the flange to cooperate with the collar in retaining the collar in fixed position on the tube.

5. In combination, a hollow tube, a collar having an inner periphery, means disposed on the collar and extending into the tube for fixedly retaining the collar on the tube, there being at least one slot in the inner periphery of the collar, a piston slidable in the hollow tube, the piston having at least one spline extending radially from the piston along the length of the piston, the piston being movable in a longitudinal direction within the tube with the spline aligned with the slot, there being at least one groove in the outer periphery of the spline, the piston being rotatable when the groove in the outer periphery of the piston becomes aligned in the longitudinal direction with the collar, and a stop on the collar for limiting the rotary movement of the piston relative to the collar and for locking the piston against movement in the longitudinal direction relative to the tube.

6. In a combination as set forth in claim 5, a flange on the tube, the collar including means extending from the collar for fixedly retaining the collar on the flange.

7. In a combination as set forth in claim 5, the collar having a portion extending inwardly from the tube to provide for the movement of the spline through the slot when the piston is moved in the longitudinal direction in the tube.

8. In a combination as set forth in claim 5, means resiliently disposed at the inner end of the piston in sealing relationship with the tube for providing for the introduction of fluid or tissue into the tube in accordance with the movement of the piston and for providing for the retention of such fluid or tissue in the tube.

9. In a combination as set forth in claim 5, means disposed in the piston for facilitating manual movement of the piston relative to the tube.

10. In a combination as set forth in claim 7, a flange on the tube, the collar including means extending from the collar for fixedly retaining the collar on the flange, the collar having a portion extending inwardly from the tube to provide for the movement of the spline through the slot when the piston is moved in the longitudinal direction in the tube.

11. In combination, a hollow tube having a cylindrical configuration, an annular collar having an annular inner periphery, means extending from the collar for fixedly retaining the collar on the tube with the inner periphery of the collar disposed below the inner periphery of the hollow tube, there being slots in the collar at the inner periphery of the collar, a piston disposed in the hollow tube and having splines extending radially outwardly for disposition in the slots in the collar, the splines having grooves at spaced positions in the axial direction to provide for a rotation of the piston when the grooves in the piston become axially aligned with the collar, and means on the collar for stopping the rotation of the piston after the piston has been rotated through a particular angle.

12. In a combination as set forth in claim 11, a sleeve made from a resilient material and disposed within the piston in close fit with the inner periphery of the hollow tube for providing a sealed compartment within the hollow tube for retaining fluid or tissue withdrawn into the tube by the axial movement of the piston.

13. In a combination as set forth in claim 11, a plurality of ramps each extending in an annular direction to an individual one of the stopping means for facilitating the rotation of the splines against the stopping means.

14. In a combination as set forth in claim 11, a radial flange on the tube, the retaining means on the collar including a lug integral with the collar at a position axially displaced from the collar by a distance greater than the thickness of the flange, the lug extending through the flange to the opposite side of the flange from the collar and being disposed against the opposite side of the flange.

15. In a combination as set forth in claim 11, means disclosed at the end of the piston removed from the hollow tube for providing for the insertion of a finger to facilitate the manual movement of the piston relative to the tube.

16. In a combination as recited in claim 12, a plurality of ramps each extending in an annular direction to an individual one of the stopping means for facilitating the rotation of the splines against the stopping means, a radial flange on the tube, the retaining means on the collar including a lug integral with the collar at a position axially displaced from the collar by a distance greater than the thickness of the flange, the lug extending through the flange to the opposite side of the flange from the collar and being disposed against the opposite side of the flange, and means disposed at the end of the piston removed from the hollow tube for providing for the insertion of a finger to facilitate the manual movement of the piston relative to the tube.

17. In combination, a hollow tube extending in a longitudinal direction, a flange extending from the tube in a direction transverse to the longitudinal direction and having opposite surfaces defining the thickness of the flange in the longitudinal direction, a collar having an open inner periphery and disposed against one of the surfaces of the flange, lugs extending through the flange and disposed against the opposite surface of the flange to retain the collar fixedly against the flange, slots extending into the collar from the inner periphery of the collar, a piston disposed in the hollow tube and extending outwardly from the tube and having splines extending in the longitudinal direction along the piston for disposition in the slots in the collar, there being grooves in the splines at the outer periphery of the splines to provide for a rotation of the piston relative to the hollow tube when the grooves in the splines become aligned in the longitudinal and rotational directions with the slots in the collar, and means disposed on the collar for limiting the rotation of the piston relative to the hollow tube after the piston has been rotated to a position where the grooves in the splines are no longer aligned in the longitudinal and rotational directions with the slots in the collar.

18. In a combination as set forth in claim 17, the hollow tube having an inner periphery, a sleeve resiliently disposed in the hollow tube at the end of the piston in sealing relationship with the interior periphery of the hollow tube.

19. In a combination as set forth in claim 18, the hollow tube having an inner periphery, the collar extending radially inwardly into the hollow tube to a position radially interior of the inner periphery of the hollow tube and the slots being disposed in the portion of the collar radially interior to the inner periphery of the hollow tube.

20. In a combination as set forth in claim 17, a handle portion on the piston at the end of the piston opposite the portion of the piston within the hollow tube for facilitating the manual movement of the piston in the longitudinal and rotational directions.

21. In a combination as set forth in claim 19, the hollow tube having an inner periphery, a sleeve resiliently disposed in the hollow tube at the end of the piston in sealing relationship with the interior periphery of the hollow tube, and a handle portion on the piston at the end of the piston opposite the portion of the piston within the hollow tube for facilitating the manual movement of the piston in the longitudinal and rotational directions.

* * * * *